United States Patent [19]

Brady et al.

[11] Patent Number: 4,733,798

[45] Date of Patent: Mar. 29, 1988

[54] METHOD AND APPARATUS FOR CONTROLLING THE CONCENTRATION OF A CHEMICAL SOLUTION

[75] Inventors: Daniel F. Brady, Eagan; Spencer B. Larson, Cottage Grove; David B. Ziegler, Eden Prairie; Charles B. Johnson, Eagan, all of Minn.

[73] Assignee: Ecolab Inc., St. Paul, Minn.

[21] Appl. No.: 826,205

[22] Filed: Feb. 5, 1986

[51] Int. Cl.$^4$ ............................................. B67D 5/08
[52] U.S. Cl. ........................................ 222/23; 222/52; 222/644; 134/113; 137/5; 137/93; 324/441; 324/445
[58] Field of Search ................. 222/23, 39, 52, 54, 222/638, 644, 57; 324/441, 445; 137/5, 93; 134/113

[56] References Cited

U.S. PATENT DOCUMENTS

| | | | |
|---|---|---|---|
| 2,370,609 | 2/1945 | Wilson et al. | 175/183 |
| 2,715,722 | 8/1955 | Relis | 340/253 |
| 3,095,121 | 6/1963 | Douty et al. | 222/52 |
| 3,253,741 | 5/1966 | Russell et al. | 222/52 |
| 3,307,744 | 3/1967 | Burford | 222/1 |
| 3,319,637 | 5/1967 | Gore et al. | 134/57 |
| 3,389,332 | 6/1968 | Ketcham | 324/445 |
| 3,595,438 | 7/1971 | Daley | 222/67 |
| 3,603,873 | 9/1972 | Ciruis | 324/445 |
| 3,680,070 | 7/1972 | Nystuen | 340/244 |
| 3,850,344 | 11/1974 | Burge et al. | 222/67 |
| 3,876,106 | 4/1975 | Powell et al. | 222/57 |
| 3,999,687 | 12/1976 | Baer et al. | 222/52 |
| 4,020,865 | 5/1977 | Moffat et al. | 137/68 |
| 4,056,470 | 11/1977 | Carpenter | 222/52 X |
| 4,063,663 | 12/1977 | Larson et al. | 222/52 |
| 4,076,146 | 2/1978 | Lausberg et al. | 222/52 |
| 4,389,972 | 6/1983 | Hirakura et al. | 222/57 X |
| 4,426,362 | 1/1984 | Copeland et al. | 422/263 |
| 4,440,314 | 4/1984 | Vetter et al. | 222/39 |

OTHER PUBLICATIONS

Instruction Book, The Foxboro Company, 1984.

Primary Examiner—Joseph J. Rolla
Assistant Examiner—Frederick R. Handren
Attorney, Agent, or Firm—Merchant, Gould, Smith, Edell, Welter & Schmidt

[57] ABSTRACT

The invention includes a method and apparatus for controlling the concentration of wash water in a ware washing machine. A preferred ware washing machine (10) includes a reservoir (11) for holding wash water, a normally closed valve (17) for directing clean water to a dry detergent supply (13), an electrodeless conductivity cell (12) for monitoring the conductivity of the ware washing solution, and a controller for activating the normally closed valve (15) in response to the difference between the measured concentration and the actual concentration. A preferred concentration controller includes an adjustable amplifier (48) which provides an amplified concentration signal which is equal to a reference signal when the concentration of the solution is equal to the desired concentration. In addition, a preferred conductivity cell (12) includes a thermistor (46) which, in effect, increases or decreases the voltage of the signal produced by the secondary coil to remove the apparent concentration changes solely associated with changes in temperature of the washing solution.

12 Claims, 7 Drawing Figures

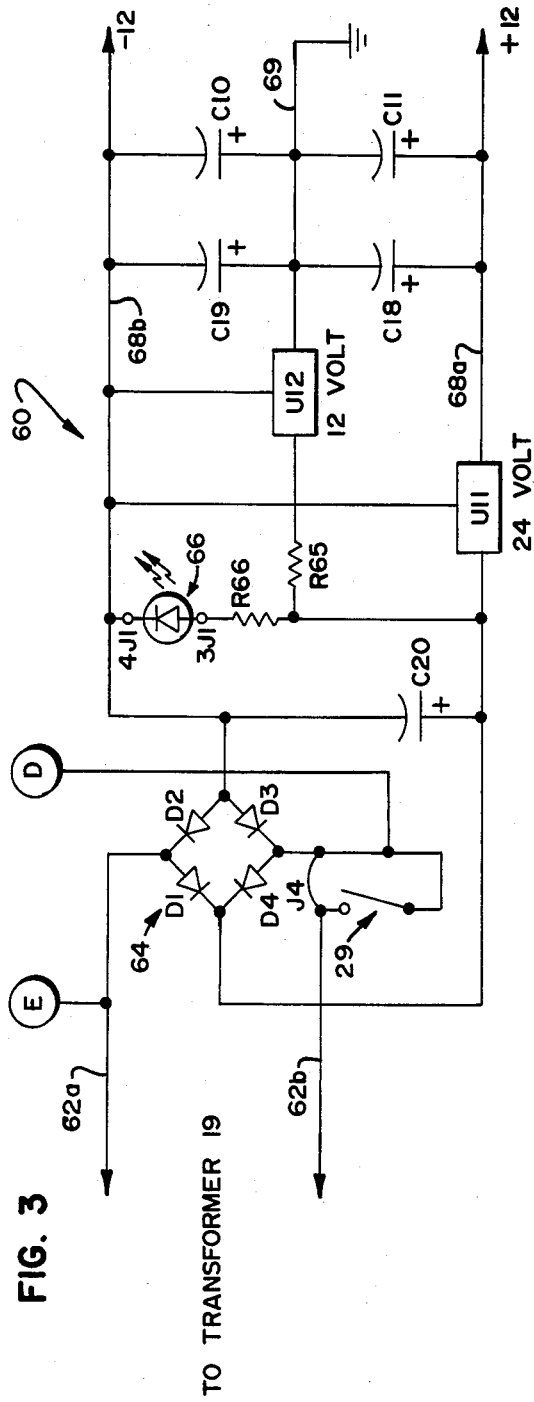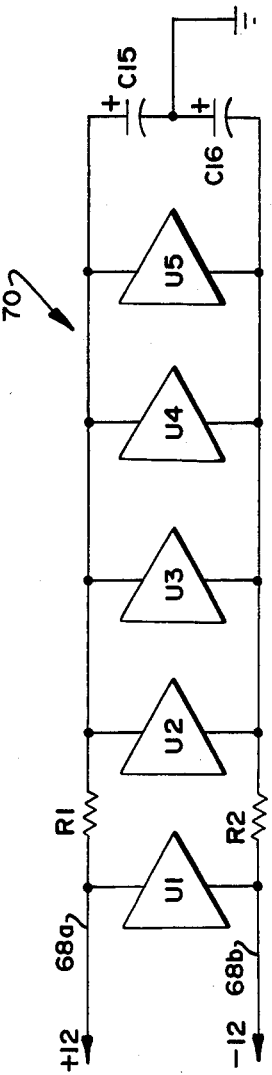
FIG. 3
FIG. 4

METHOD AND APPARATUS FOR CONTROLLING THE CONCENTRATION OF A CHEMICAL SOLUTION

FIELD OF THE INVENTION

This invention relates generally to methods and apparatus for controlling the concentration of a chemical solution. More particularly, the invention relates to methods and apparatus for controlling the concentration of a chemical solution for measuring the conductivity of the solution and taking appropriate corrective action.

BACKGROUND OF THE INVENTION

Chemical solutions are used for a variety of purposes, and it is often necessary to control the concentration of a chemical solution to achieve a particular goal. For example, the concentrations of chemical solutions must sometimes be maintained in industrial processing plants. As another example, chemical cleaning apparatus often employ chemical solutions which must have certain concentrations to be most effective. Although the concentration controlling apparatus and method of the present invention can generally be used to control the concentration of any chemical solution, the present invention is primarily directed to the automatic control of the concentration of a chemical cleaning solution. Therefore, the following discussion focuses on chemical cleaning solutions and their control and even more particularly focuses on controlling the concentration of cleaning solutions used in institutional ware washing machines. However, it should again be stressed that the concentration controller of the present invention is not limited to chemical cleaning solutions nor is it limited to the ware washing setting described herein.

Certain commercial dishwashers such as those used in hotels, restaurants, hospitals and other large organizations have a reservoir in which dishwashing water containing detergent is stored. In use of such dishwashers, this water is pumped from the reservoir to wash the dishes during a washing cycle and the water in the reservoir is not fully changed at the end of washing each load of dishes, but is used again for the next load of dishes. Further, such dishwashers have a rinsing cycle in which fresh water is delivered to rinse them and the runoff of fresh water passes through the reservoir and causes a partial change thereof. Food soil and rinse water can cause the concentration of detergent in the wash water to drop unacceptably low.

The utilization of automatic dispenses to control the concentration of chemical solutions used in ware washing or dishwashing machines is well-known in the art. Such automatic dispensers may generally be placed in two broad categories based upon their method of controlling the amount of chemical dispensed: (1) time controlled dispensers, and (2) conductivity measurement dispensers.

Time controlled dispensers dispense solvent or chemicals for a predetermined period of time. They do not monitor the concentration of the cleaning solution to determine whether there should be more or less solvent or chemical delivered during a given cycle.

In conductivity measurement controllers, on the other hand, a conductivity cell normally monitors the amount of detergent in the wash water, and when the detergent concentration falls below a desired level, the conductivity controller produces a signal which opens a valve to add more detergent or concentrated detergent solution to the wash water. The present invention is primarily directed to apparatus which measure the conductivity of the cleaning solution (wash water) and act accordingly to maintain an optimum concentration.

Prior art conductivity cells generally include a pair of bare metal electrodes immersed in the cleaning solution. For example, U.S. Pat. Nos. 3,253,741 and 3,680,070 disclose such conductivity cells. Although such systems are generally useful for their intended purposes, it is perceived that they possess several shortcomings. For example, the bare metal electrodes of electrode-type conductivity cells are subject to scumming. That is, the electrodes can be coated by a film when they are used to monitor a hard water solution, a some films can erroneously indicate an acceptable high conductivity when in fact the conductivity, and therefore the concentration of the cleaning solution is unacceptably low. Similarly, food soil in the wash water and some films can cause bare metal electrodes to indicate an artificially high conductivity. Scummed electrodes must be periodically cleaned or replaced to maintain their accuracy within acceptacle limits.

In addition, temperature compensation in electrode-based systems presents a problem. Generally a third sensor e.g, a thermistor is separately immersed in the wash water.

Also, some prior art concentrations controllers temporarily overcompensate for a low detergent condition, thereby causing the concentration to overshoot the set point.

The present invention is directed to a concentration controller which employs an electrodeless sensor. This type of controller addresses the shortcomings of the prior art concentration controllers: First, an electrodeless conductivity sensor or cell reduces maintenance since scumming of bare metal electrodes is eliminated. Secondly, the accuracy of the concentration controller is enhanced, being substantially unaffected by food soil, fluctuating water hardness or fluctuating temperatures. Thirdly, a temperature compensation transducer can be readily included as an integral part of the electrodeless cell to eliminate the need for a separate temperature transducer. Finally, a preferred controller includes means for substantially eliminating the overshoot problem discussed above.

SUMMARY OF THE INVENTION

Accordingly, the present invention includes an apparatus for controlling the concentration of a solution including:

(a) a primary coil and a secondary coil; wherein when the coils are immersed in the solution the solution provides an electrical coupling between the coils;

(b) means for changing the concentration of the solution;

(c) means for controlling the concentration changing means including:
  (i) means for comparing the concentration signal with a reference signal representing a preselected desired concentration and generating an error signal representing the difference therebetween; and
  (ii) means for activating the concentration changing means in response to the error signal; and (d) alarm means for determining whether the concentration changing means has been excessively activated.

A preferred concentration controlling apparatus also includes means for compensating for changes in the temperature of the solution so that apparent changes in the concentration due solely to temperature changes are effectively removed or filtered.

The temperature compensating means preferably includes a thermistor which is immersed or otherwise placed in thermal contact with the solution. The thermistor is connected to the secondary coil such that the signal produced by the secondary coil is decreased with an increase in solution temperature and the concentration signal is increased with a decrease in the solution temperature. Thus, apparent concentration changes caused by changes in the solution temperature are not reflected in the concentration signal.

The concentration changing means mentioned above preferably includes means for increasing the concentration of the solution. Also, the activating means discussed above preferably includes timing means for:

(a) continuously activating the concentration increasing means when the error signal indicates that the concentration of the solution is less than a preselected percentage of the desired concentration;

(b) not activating the concentration increasing means when the error signal indicates that the concentration of the solution is substantially equal to the desired concentration; and (c) periodically activating the concentration increasing means when the error signal indicates that the concentration of the solution is between the desired concentration and the preselected percentage of the desired concentration, wherein the rate at which the concentration increasing means is activated is directly related to the difference between the actual concentration and the desired concentration, whereby overshoot is substantially eliminated.

The timing apparatus preferably includes a capacitor which is charged by the error signal provided by a comparator. The concentration increasing means is not activated during the period of time that the capacitor is charging, whereby the concentration increasing means (e.g., a normally-closed valve) is not activated for a period of time directly dependent on the magnitude of the error signal, and is otherwise activated.

The apparatus also preferably includes an adjustable amplifier or the like which can be adjusted so that the concentration signal is equal to the reference signal when the measured concentration is equal to the desired concentration. An op amp, for example, can be used for the adjustable amplifier, wherein the gain of the op amp can be adjusted by selecting various combinations of feedback resistors.

The reference signal generated by the apparatus preferably includes a first reference signal representing 100% of the desired concentration and a second reference signal representing a preselected lower percentage of the desired concentration. Also, the comparing means preferably includes first and second comparators for comparing the first and second reference signals to the concentration signal provided by the secondary coil (and preferably temperature compensated). When the second comparator indicates that the measured concentration is less than the preselected lower percentage of the desired concentration, the concentration changing means is preferably continuously activated; when the second comparator indicates that the measured conductivity is greater than the preselected lower percentage of the desired concentration and the first comparator indicates that the measured concentration is less than the desired concentration, the activating means periodically activates the concentration changing means at a rate which is directly related to the magnitude of the error signal; and when the first comparator indicates that the concentration of the solution is substantially equal to the desired concentration, the activating means does not activate the concentration changing means.

Preferably, the preselected lower percentage discussed above is 90% of the desired concentration.

Preferably, the concentration controlling apparatus is for controlling the wash water solution of a ware washing machine. Such a concentration controller would preferably control the flow of a concentrated solution of detergent and water to the wash water solution in response to the error signal.

The invention also includes a washing machine which includes means for containing the wash water solution.

Finally, the invention includes a method for controlling the concentration of a solution including:

(a) immersing a primary coil and a secondary coil in the solution in such a way that the solution provides an electrical coupling between the coils;

(b) energizing the primary coil to produce a concentration signal in the secondary coil;

(c) producing a reference signal representing a preselected desired concentration;

(d) comparing the concentration signal to the reference signal to generate an error signal representing the difference therebetween;

(e) changing the flow of the concentrated detergent solution in response to the error signal; and (f) activating an alarm when the error signal indicates an excessive difference between the measured concentration and the desired concentration for an excessive period of time.

BRIEF DESCRIPTION OF THE DRAWINGS

The invention is further described with reference to the accompanying drawing in which:

FIG. 3 is a circuit diagram of a preferred power supply for the controller of FIG. 1;

FIG. 4 is a circuit diagram illustrating the preferred distribution of DC power from the power supply of FIG. 3 to several active components of the controller;

DESCRIPTION OF A PREFERRED EMBODIMENT

Figure 1:
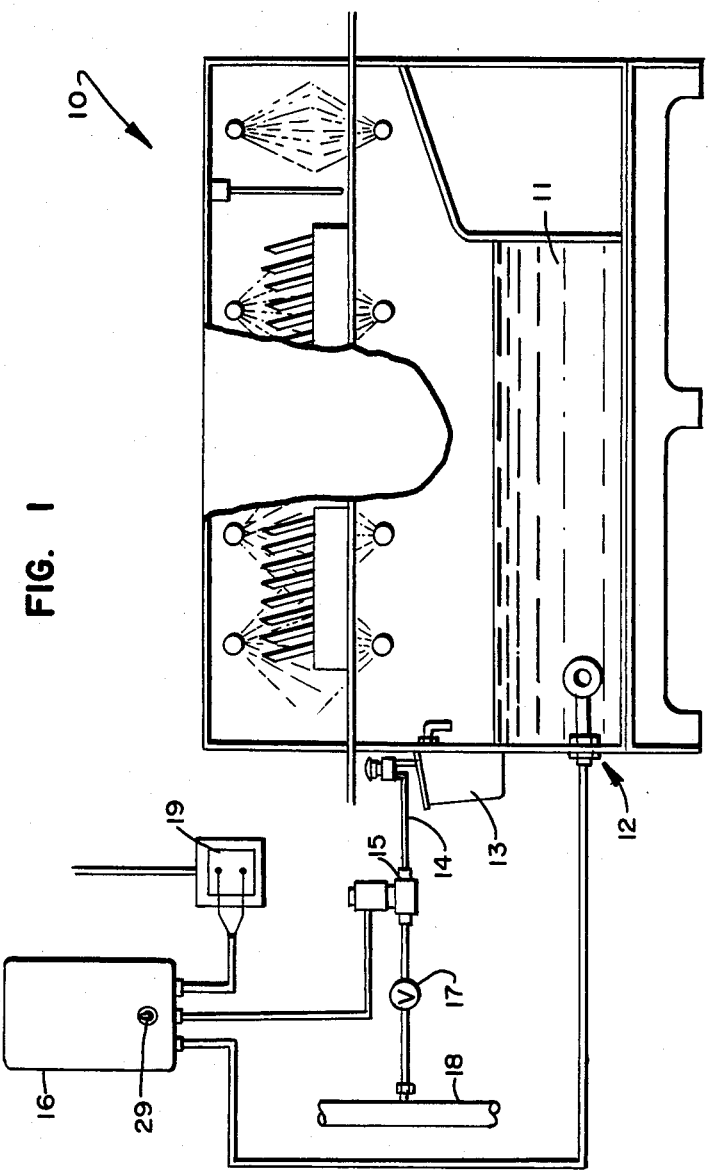
FIG. 1 is a diagrammatic view of a dishwashing unit including a wash water concentration controller of the present invention.

Referring to the drawing, wherein like reference numerals indicate like parts throughout the several views, FIG. 1 shows a dishwasher 10 having a solution tank 11 at the bottom thereof with a conductivity cell 12 affixed in one wall so that the sensing portion thereof is positioned within a solution within the solution tank 11. A reservoir 13 positioned, for example, externally on a side wall generally above the level of the solution in the tank 11 contains some material, such as a detergent or the like. A water line 14 conducts water to the reservoir 13, when desired, to cause the reservoir 13 to overflow into the solution tank 11 and raise the concentration of the detergent solution in the tank 11.

It should be noted at the outset that the concentration control system of the present invention is not limited to the washing apparatus illustrated in FIG. 1. The mechanical aspects of the washing apparatus 10 in particular are shown only by way of example and these mechanical components could readily be replaced by similar components as well known to those skilled in the art of institutional washing machines. The reservoir 13, for example, could be replaced by any of a large variety of detergent dispensers; reference is made to U.S. Pat. No. 4,063,663, issued to Larson et al, the contents of which are incorporated herein.

Still referring to FIG. 1, a normally closed solenoid valve 15 is connected to mechanically control the flow of water in the water line 14 and is electrically connected to a control unit 16. The water line 14 preferably has a manual type control valve 17 which controls the flow of water in the line 14 for purposes of maintenance, etc. The water line 14 is connected to a water supply line 18, which is in turn connected to a source of water (not shown).

The control unit 16 is connected to a suitable source of power, such as 115 Volts AC, through a transformer 19. The transformer 19 reduces the voltage applied to the control unit 16 to some suitable amplitude, such as 24 Volts AC. An on/off switch 29 can be provided on controller 16.

The electrodeless conductivity cell is of the type having a primary coil, a secondary coil and a temperature compensation sensor imbedded in a toroidal plastic sheath. The sheath is preferably food grade polypropylene. The Foxboro Company, Foxboro, Mass., for example sells such conductivity cells. The liquid in the cylindrical hole formed by the toroidally shaped sensor forms the core of a transformer formed by the primary and secondary coils, and the conductivity of the core solution directly affects the coupling between the coils.

Figure 2:
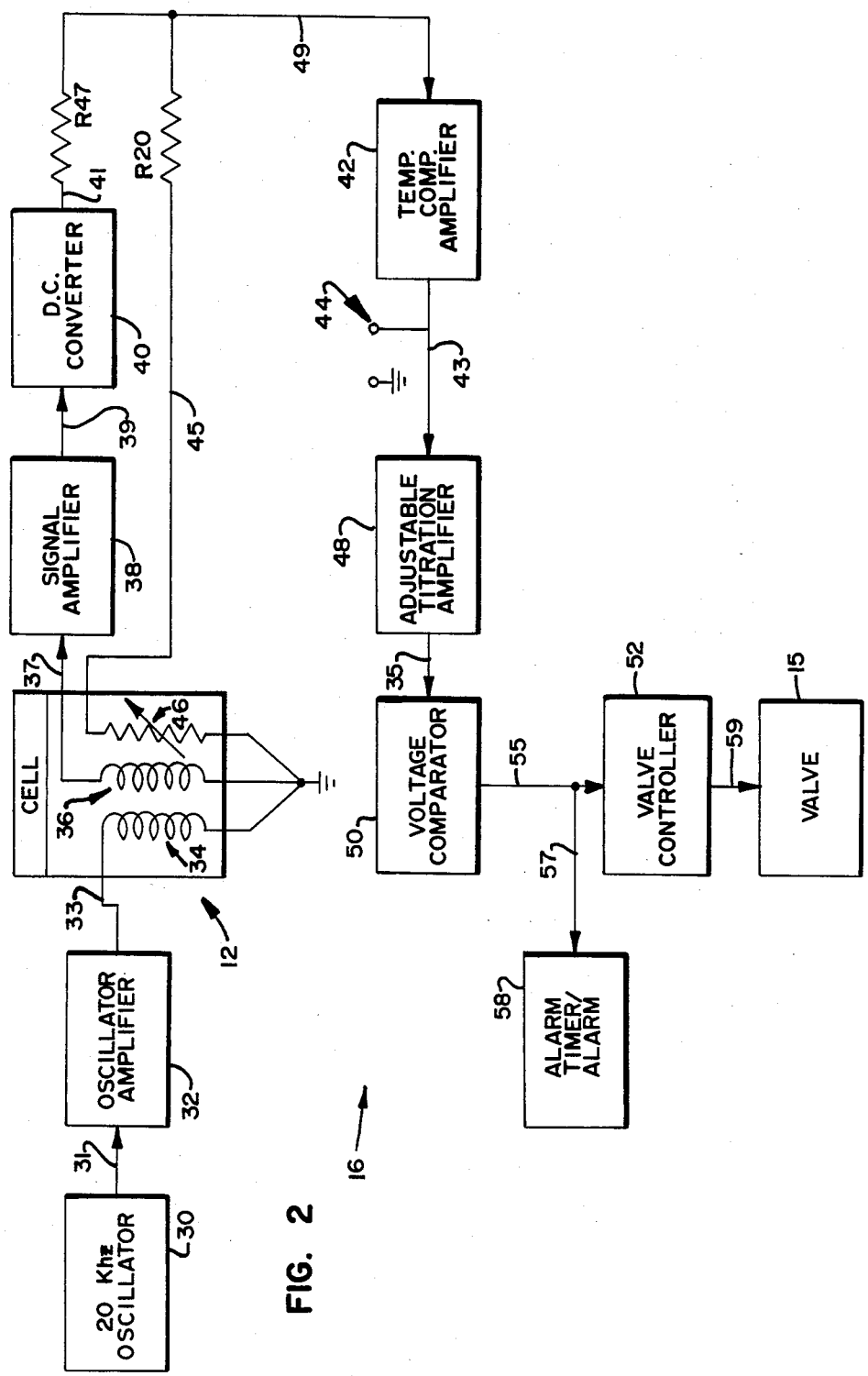
FIG. 2 is a functional block diagram of a preferred embodiment of the concentration controller of FIG. 1.

FIG. 2 shows a schematic or functional diagram of a preferred circuit for the control unit 16. Starting in the upper left hand corner of the schematic, the preferred control unit 16 includes a 20 Khz oscillator 30. The oscillator 30 is connected to an oscillator amplifier 32 by signal flow path 31. The output of amplifier 32 is supplied via signal flow path 33 to the first terminal of a primary coil 34 imbedded within the conductivity cell 12. The second terminal of the primary coil 34 is connected to circuit common. A secondary coil 36 also imbedded in the conductivity cell 12, the first terminal of the secondary coil 36 being connected to a signal amplifier 38 by flow path 37, and the second terminal of the secondary coil 36 being connected to circuit common. The voltage induced in the secondary coil 36 is amplified in the signal amplifier 38 and converted to DC in a DC converter 40 connected to the signal amplifier 38 by a signal flow path 39. The resulting DC signal is amplified by a temperature compensation amplifier 42 (connected to DC converter 40 by a signal flow path consisting of flow path 41, resistor R47 and flow path 49) and the amplified output of amplifier 42 is available at test point 44 as a temperature compensated DC signal proportional to the concentration of the detergent in the wash water contained within tank 11.

Temperature compensation is provided by a variable voltage divider network made up of resistors R47 and R20 and temperature compensation thermistor 46 preferably imbedded within conductivity cell 12. Resistor R47 lies between DC converter 40 and the input of temperature controller amp 42, and resistor R20 and thermistor 46 are in series and interconnect the input of temperature controller amplifier 42 and ground. As further described below, as the temperature of the wash water increases the resistance of thermistor 46 decreases to reduce the level of the DC input signal provided to the input of temperature compensation amplifier 42. Similarly, a decrease in temperature causes an increase in the DC input to amplifier 42.

The output of temperature compensation amplifier 42 is fed through a signal flow path 43 to an adjustable titration amplifer circuit 48. As further described below, the gain of amplifier 48 is manually adjustable, in a unique manner, so that the concentration set point of the control unit 16 can be readily adjusted to a large variety of values. The control unit 16 attempts to maintain the level of the output of amplifier 48 at a voltage representative of the set point.

The input of a voltage comparator circuit 50 is connected to the output of the titration amplifier 48 by a signal flow path 35. The output of comparator 50 is in turn connected via flow path 55 to a valve controller circuit 52 which is connected to the valve 15. The voltage comparator 50 compares the output of titration amplifier 48 to a pair of reference voltages to determine whether and how often to activate the valve controller 52.

Finally, a flow path 57 connects an alarm timer circuit 48 to the voltage comparator 50 and the valve controller 52. The alarm timer 58 activates an alarm if the feed valve is on for too long, indicating a lack of detergent in the detergent dispenser, for example. The basic components or subcircuits of preferred control unit 16 having been introduced, detailed circuit diagrams will now be discussed.

FIG. 3 illustrates a DC power supply circuit 60 which can be used in conjunction with the control unit 16. The power supply 60 is not shown in FIG. 2 as a matter of convenience, but is it understood that the various subcircuits of control unit 16 are preferably supplied with regulated DC power.

The power supply 60 includes a pair of AC input terminals 62a and 62b. Terminals 62 are operatively connected to transformer 19 (shown in FIG. 1) and supply the 24 Volt AC output of transformer 19 to a full wave diode rectifier 64. Rectifier 64 includes four diodes, D1–D4, with the p regions of diodes D2 and D3 and the n regions of diodes D1 and D4, respectively, being tied together. The output terminals of the rectifier 64 are the junctions between diodes D2 and D3 and diodes D1 and D4, respectively.

Terminals 62 are also connected to valve controller subcircuit 52 (shown in FIG. 5C) so that the 24 Volt AC power can be selectively provided to solenoid valve 15. Referring again to FIG. 3, it should be noted that a jumper J4 normally defeats the switch 29 (also shown in FIG. 1) so that 24 Volt AC power is normally continuously supplied to the controller 16. However, if jumper J4 is removed switch 29 is enabled.

The output terminals of full wave rectifier 64 are connected across a capacitor C20, the function of C20 being to smooth the rectified AC power signal. The DC voltage across capacitor C20 will be approximately 35 Volts DC.

The output terminals of full wave rectifier 64 are also connected across a LED 66 and a resistor R66 connected in series. LED 66 is energized when rectified power is provided by the full wave rectifier 64, and thus serves as an "on" light for the controller 16. LED 66 is preferably mounted to be visible on the outside cabinet of controller 16. DC power regulators U11 and U12 supply regulated plus and minus 12 Volts DC according to well-known principles. DC regulator U11, a 24 Volt DC regulator, has one terminal in common with the positive plate of capacitor C20; one terminal 68b in common with the negative plate of capacitor C20; and a third terminal 68a providing positive 12 Volts DC. The 24 volt regulator U11 serves to maintain a 24 Volt DC difference between the terminal 68a and 68b.

One terminal of the regulator U12 is connected through a resistor R65 to the positive plate of capacitor C20; another terminal serves as a ground terminal 69; and the third terminal is tied to terminal 68b. The regulator U12 maintains a 12 Volt DC difference between the voltage on the ground terminal 69 and the voltage on terminal 68b, thereby in effect centering the DC output of power supply 60 about ground potential. Finally, a pair of parallel capacitors C19 and C10 span between the minus 12 terminal 68b and the ground terminal 69; and a pair of parallel capacitors C18 and C11 connect the ground terminal 69 to the plus 12 terminal 68a. Capacitors C10, C11, C18 and C19 serve to filter out transients on the terminals 68 and 69.

As shown in FIG. 4, the plus and minus 12 Volt DC power produced by power supply 60 is provided to a series of operational amplifiers U1–U5 according to a power distribution circuit 70. The power supply lines for these op amps are not shown in the remaining circuit diagrams, but it is understood that all of the integrated circuits are supplied with regulated DC power. Resistors R1 and R2 and capacitors C15 and C16 are included in the power distribution circuit 70. Resistors R1 and R2 isolate, to some degree, op amp U1 from the remaining op amps U2–U5 so that the oscillator function performed by op amp U1 does not adversely affect the performance of op amps U2–U5 via small oscillations on the regulated power supply lines. The capacitors C15 and C16 tie terminal 68a and terminal 68b to ground, respectively.

Of course, all of the integrated circuits of controller 16 are provided with regulated DC power, whether or not they are op amps. And, some of the op amps of controller 16 are not respresented in FIG. 4; this diagram is intended merely to show how the power is generally supplied to the integrated circuits, and of course all of the op amps are appropriately supplied.

Figure 5A:
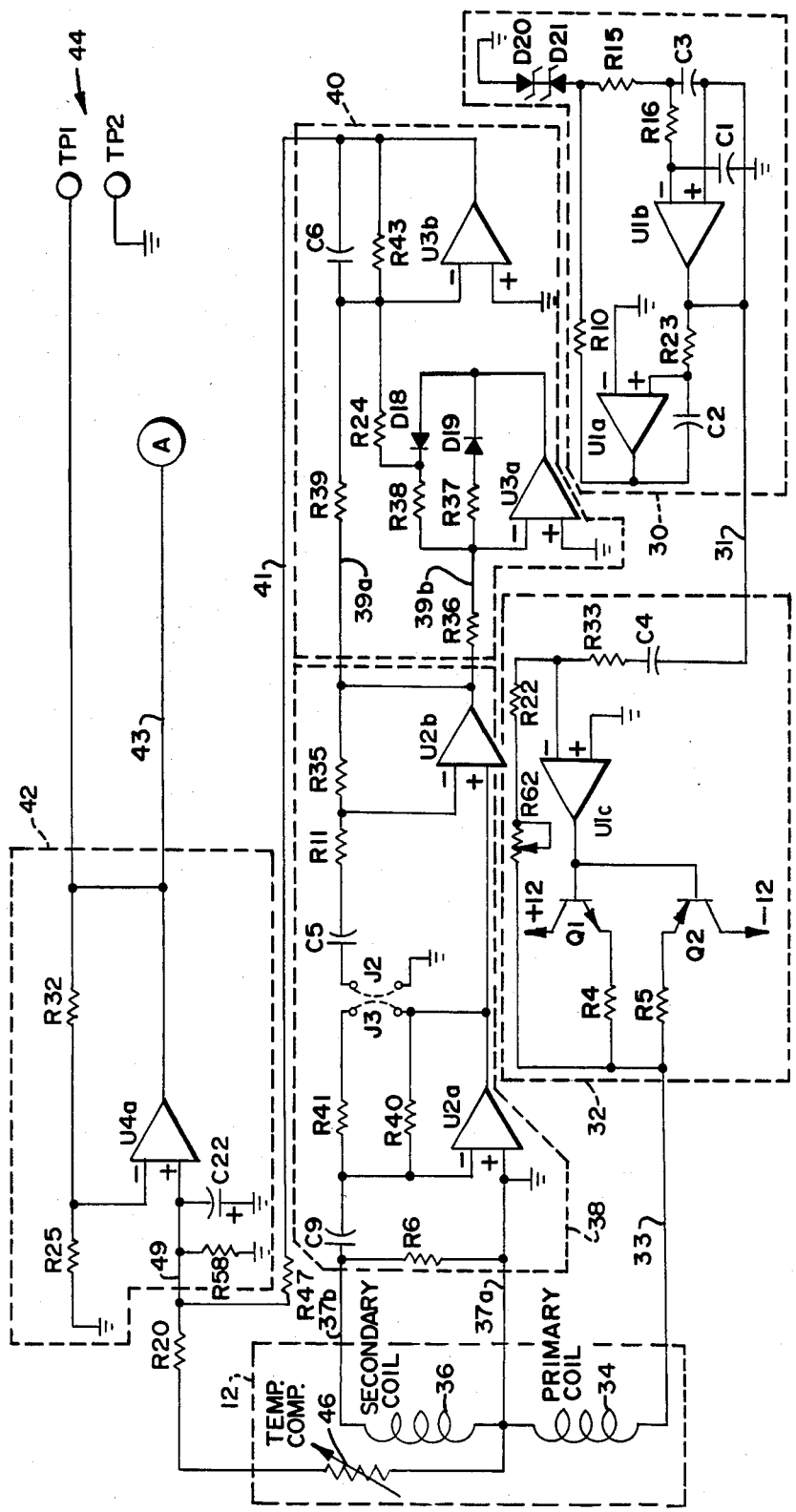
FIG. 5A is a circuit diagram illustrating a first portion of a preferred concentration controller of the type functionally diagrammed in FIG. 2.

FIG. 5A shows a circuit diagram of several subcircuits of the preferred control unit 16, including the 20 Khz (nominal) oscillator 30, oscillator amplifier 32, conductivity cell 12, signal amplifier 38, DC converter 40 and temperature compensation amplifier 42.

Oscillator 30 preferably includes a pair of op amps U1a and U1b wherein the output of op amp U1b is connected to the noninverting (+) input of op amp U1a through a resistor R23. Feedback is provided to op amp U1a by a capacitor C2 which interconnects the output and noninverting input terminal thereof, and its inverting input (−) is grounded. The output of op amp U1a is also connected to the inverting input of op amp U1b through a series of resistors R10, R15 and R16. The noninverting input terminal of op amp U1b is directly connected to the output of op amp U1b and the junction of resistors R15 and R16 is also connected to the output of op amp U1b through a capacitor C3. Finally, a capacitor C1 is connected between the inverting input terminal of op amp U1b and ground, and a pair of opposing Zener diodes D20 and D21 (n regions adjacent) clamp the junction of resistors of R10 and R15 to ground. The resulting circuit is a standard sine wave oscillator and the values of the components are selected so that the oscillator 30 provides roughly a 20 Khz AC signal. The output of oscillator 30 is taken off of the output terminal of op amp U1b, and the line 31 connects oscillator 30 to the input of the oscillator amplifier 32.

The oscillator amplifier 32 will now be described. The output of op amp U1b is connected to the inverting input of op amp U1c through a capacitor C4 and an input resistor R33 connected in series. The noninverting terminal of op amp U1c is grounded and the output of op amp U1c is connected to the bases of a pair of power transistors Q1 and Q2, wherein transistor Q1 is an NPN transistor and Q2 is a PNP transistor. The collectors of transistors Q1 and Q2 are connected to the positive and negative 12 volt power supplies, respectively. The emitters of power transistors Q1 and Q2 are connected to resistors R4 and R5, respectively. Resistors R4 and R5 form feedback loops for the amplifier 32 along with a potentiometer R62 and a resistor R22. That is, one terminal of each resistor R4 or R5 is connected to its respective transistor Q1 or Q2, and the remaining terminals of resistors R4 and R5 are tied together and connected in series with the potentiometer R62 and the resistor R22 to provide a feedback path to the inverting input of op amp U1c. Thus, op amp U1c and power transistors Q1 and Q2, along with their passive components, form a push-pull amplifier for the 20 Khz signal provided by oscillator 30.

The amplified oscillator signal is carried by line 33 to one terminal of the primary coil 34 imbedded within the electrodeless conductivity cell 12. The primary coil 34 is preferably a ferrite toroidial inductor having twenty-five turns, having an outside diameter of approximately 1.25 inch and having an inside diameter of 0.75 inch. The design and fabrication of electrodeless conductivity sensors are well known and need not be discussed in detail. The other terminal of the primary coil 34 is connected through line 37a to ground (on controller 16).

As is well known, the electrodeless conductivity cell 12 also includes a secondary coil 36 which is imbedded within the plastic covering of cell 12 and inductively coupled to the primary coil 34. The core of the resulting "transformer" includes the water within tank 11 and the coupling between the coils 34 and 36 is directly affected by the conductivity of the wash water. The secondary coil preferably has twenty-five turns but is otherwise substantially identical to the primary coil 34.

One terminal of the secondary coil 36 is grounded through line 37a and one terminal is connected via line 37b and input capacitor C9 to the inverting input of op amp U2a of signal amplifier 38. Actually, the nongrounded secondary coil terminal is connected to the negative inverting terminal of the amp U2a through a filter network made up of a resistor R6 and the capacitor C9. Resistor R6 shunts the terminals of the secondary coil 36 to remove low frequency noise or drift. Capacitor C9, interposed between the non-grounded terminal of the secondary coil 36 and the inverting input of the op amp U2a, acts as a static filter (short to AC; open to DC) and is specifically chosen to pass 20 Khz. The output of amplifier U2a is normally fed back to the inverting input of op amp U2a through a pair of parallel feedback resistors R40 and R41. The gain of op amp U2a can be increased by removing a jumper J3 to increase the feedback resistance by eliminating the effect of the resistor R41.

The output of op amp U2a is also connected to the noninverting input terminal of another op amp U2b. The output of op amp U2b is connected to its inverting input terminal via a feedback resistor R35. The output of op amp U2b is also normally tied to ground through resistors R35 and R11 and a capacitor C5. A jumper J2 can be removed to eliminate this ground connection.

Preferably, the open loop gain of op amp U2a is approximately 1,000 and the gain of op amp U2b is adjusted to be approximately 5 so that the effective gain of signal amplifier 38 is on the order of 5,000.

The amplified signal from the secondary coil 36 is then directed through line 39 to a true full wave rectifier 40. Rectifier 40 is of standard design: The output of op amp U2b of signal amplifier 38 is connected to the inverting input of an op amp U3a through an input resistor R36. The noninverting terminal of op amp U3a is grounded. The output of op amp U3a is fed back to the inverting input of op amp U3a through a parallel diode/resistor network. One leg of the network comprises a backward facing diode D19 followed by a resistor R37. The other leg of the network is preferably made up of a forward facing diode D18 followed by a resistor R38.

The junction between diode D18 and resistor R38 is connected to the inverting input of another op amp U3b through an input resistor R24. The noninverting input terminal of op amp U3b is grounded. The output of op amp U3b is returned to its inverting input terminal through a resistor R43 and capacitor C6 set in parallel. Finally, the inverting input terminal of op amp U3b is connected to the output terminal of op amp U2b through feedback resistor R39.

The true full wave rectifier 40 serves to convert the amplifed secondary coil signal to a true DC signal representative of the conductivity of the wash water coupling the primary and secondary coils 34 and 36, respectively, of cell 12.

The output of the DC converter 40, taken from the output of op amp U3b, is supplied through line 41, resistor R47 and line 49 to the temperature compensation amplifier 42. More specifically, the output of DC converter 40 is connected, through resistor R47, to the noninverting input terminal of an op amp U4a in the temperature controlling amplifier 42. The noninverting input terminal of op amp U4a is also grounded through a parallel network of a resistor R58 and a capacitor C22. In addition, the noninverting input terminal of op amp U4a is connected to the thermistor 46 imbedded in the conductivity cell 12 via the resistor R20. Thus, resistors R47, R20 and R58 and thermistor 46 form a variable voltage divider which serves to reduce the voltage at the noninverting input terminal of op amp U4a with a increase in wash water temperature. Thermistor 46 has been chosen to have a one percent change in resistance for every one degree Fahrenheit change in temperature. Thus, for example, if the temperature of the wash water increases by ten degrees Fahrenheit of the resistance of thermistor 46 will decrease approximately by ten percent. The components of the voltage divider are selected to reduce the voltage at the noninverting input of op amp U4a to compensate for changes in conductivity caused solely by changes in the temperature of the wash water.

The temperature compensated DC signal is amplified by temperature compensation amplifier 42. The output terminal of op amp U4a is returned to its inverting input terminal through feedback resistor R32 and the inverting input terminal is also connected to a resistor R25 which is grounded. As is well known, the magnitudes of resistors R32, R25, and the input resistors can be chosen to preselect the gain of op amp U4a, and for the preferred embodiment the gain of amplifier 42 is selected to be approximately 2.3.

The output of temperature compensation amplifier 42 is a DC signal directly proportional to the temperature compensated conductivity of the wash water in reservoir 11. This output signal is available for testing at test point 44 shown in FIG. 5A and also shown in FIG. 2. This output signal is also provided via line 43 to the adjustable titration amplifier circuit 48 shown in FIG. 5B. The signal is delivered to the inverting input terminal of an op amp U4b through an input resistor R19. The noninverting input terminal of op amp U4b is grounded. The feedback for op amp U4b is provided by a resistor network 80. Resistor network 80 is preferably partially made up of a feedback resistor R48 which ties the output of amplifier U4b to its inverting input terminal. In parallel with feedback resistor R48 is preferably a network of switches and resistors made up of eight parallel legs. Each leg preferably includes a resistor and a two terminal switch so that when the switch is closed its associated resistor is placed in parallel with feedback resistor R48. The bank of eight switches is preferably provided by a dip switch. Each switch of the dip switch is placed in series with one of the following feedback resistors: R21, R34, R42, R46, R53, R54, R56 and R59. The values of the selectable feedback resistors are chosen for a specific purpose as further described below.

The output of the temperature compensation amplifier 42 is a signal which varies between approximately 0.25 Volt DC and 5 Volts DC depending on the temperature compensated conductivity of the wash water in reservoir 11. It is desirable to amplify the output of temperature compensation amplifier 42 to 5 volts when the conductivity of the wash water is 100% of its preselected value. Thus, the gain of the titration amplifier 48 must be manually selected when the appropriate conductivity for the wash water is chosen. The switch/resistor network 80 allows for this manual gain adjustment of titration amplifier 48. When none of the switches of the feedback network 80 is closed the gain of the titration amplifier is preferably substantially 20. This gain results in a 5 volt signal at the output terminal of op amp U4b when the output of temperature compensation amplifier 42 is 0.25 Volt DC. 0.25 Volt DC has been selected as the minimum control voltage; when no detergent is present in the wash water, the output of amplifier 42 is approximately 0.25 Volt DC.

If it is desired to have the temperature compensated set point correspond to a higher conductivity, the gain of titration amplifier 48 must be decreased. If the switch associated with feedback resistor R59 is closed, the effective feedback resistence of op amp U4b is the parallel combination of resistors R48 and R59. This causes the gain of the titration amplifier 48 to change from approximately 20 to 18. Similarly, if the switches associated with resistors R56 and R59 are closed, while keeping the other feedback switches open, the gain changes from approximately 18 to 15.

Therefore, if the temperature compensated conductivity of the wash water in reservoir 11 is equal to the preselected conductivity, the voltage at the output terminal of op amp U4b will be equal to 5 Volts DC. The output of op amp U4b (the output of titration amplifier 48) is connected by line 35 to the voltage comparator 50. The line 35 connects the output of the op amp U4b to the noninverting input terminals of op amps U5a and U5b through resistors R45 and R26, respectively. A 5 Volt DC reference signal is provided to the inverting input of op amp U5a and a 4.5 volt reference signal is provided to the inverting input of op amp U5b in the following manner: The inverting input terminal of op amp U5a is connected to the plus 12 Volt DC power bus through a resistor R44, a potentiometer R61 and a resistor R12, in series. The junction between resistor R44 and potentiometer R61 is also connected through resistor R8 to the inverting input of op amp U5b. The inverting input of op amp U5b is also connected to ground through a capacitor C21 and a resistor R18, in parallel. A Zenor diode D22 connects the junction of potentiometer R61 and resistor R12 to ground, wherein the n region of Zenor diode D22 is adjacent the above-mentioned junction.

The noninverting input of op amp U5a is grounded through a resistor R50. The output of op amp U5a is fed back to its inverting input terminal through a forward facing feedback diode D16. The inverting input terminal of op amp U5a is also connected to ground through a resistor R49 and a resistor R27, in series.

The feedback for op amp U5b is provided between its output and its noninverting input terminal via resistor R68.

The junction between resistors R27 and R49 is connected to the emitter of a PNP transistor Q5. The emitter of Q5, the collector of Q5 and the output terminal of op amp U5b are connected to the valve controller 52a by signal flow path 55.

Figure 5B:
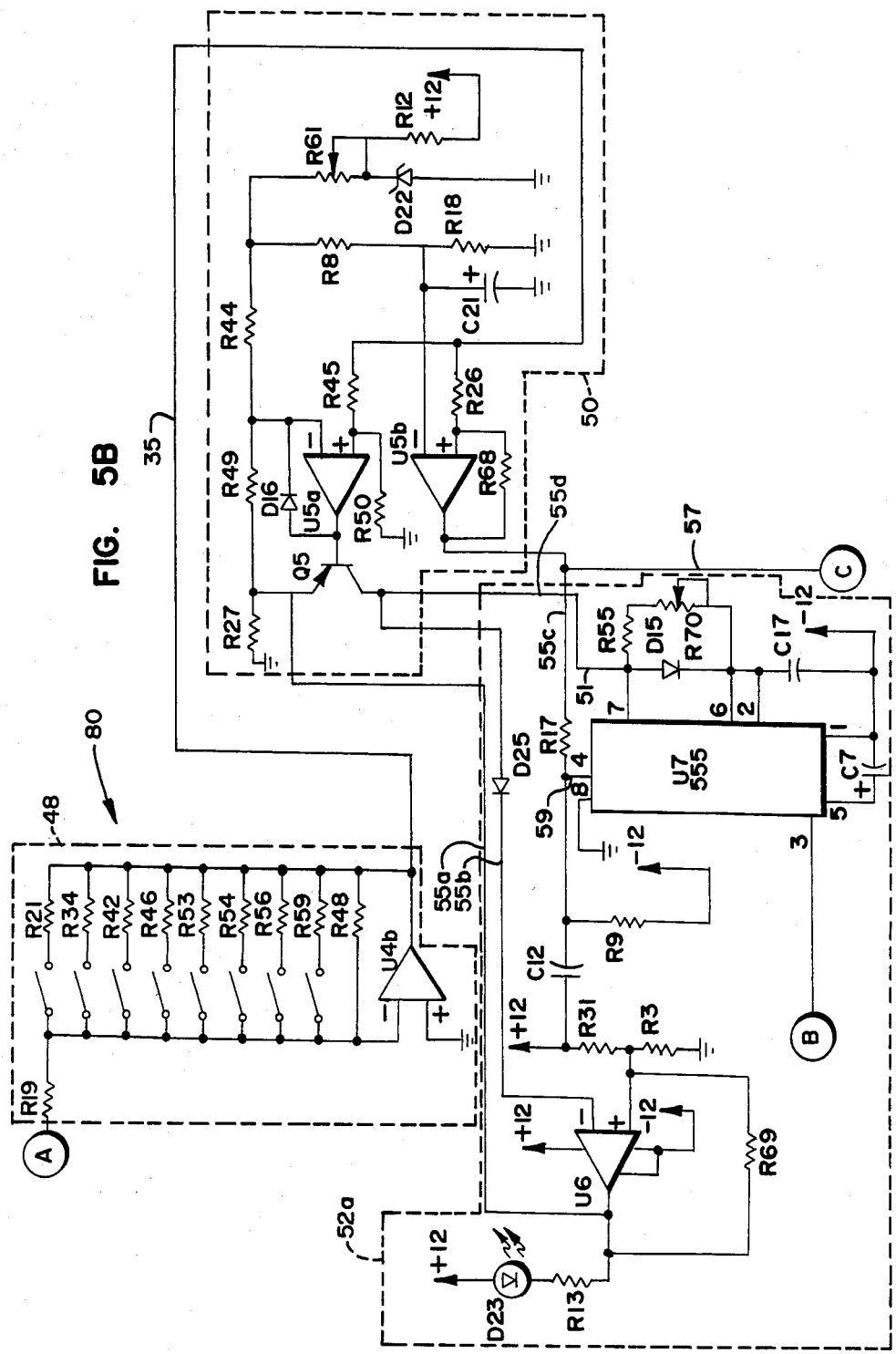
FIG. 5B is a circuit diagram illustrating a second portion of a prferred concentration controller of the type functionally diagrammed in FIG. 2.

The valve controller 52 will now be described with initial reference to FIG. 5B. The primary component of the valve controller 52 is a type 555 integrated circuit timer U7. The timer 47 can be overridden if the concentration is less than 90% of the set point, in which case the solenoid valve 15 will be activated and maintained in its activated state. If the concentration is between 90% of the set point and 100% of the set point, the timer U7 modulates the off time of the valve 15 so as to periodically feed detergent or detergent solution to the wash water in reservoir 11. Of course, if the measured concentration is 100% of the set point, the valve 15 is not activated. The important pin numbers of timer U7 are shown in FIG. 5B and these numbers will be referenced during the discussion of valve controller 52.

In addition to the integrated timer U7, the valve controller 52 includes a diode D15 connected via line 55d to the collector of the transistor Q5 of comparator 50. The p region of diode D15 is common to the collector of transistor Q5. On the n side of diode D15 is a capacitor C17 with the other terminal of capacitor C17 being connected to the minus 12 volt power supply. The junction between diode D15 and capacitor C17 is connected to pin 2 of the integrated timer U7. The junction between diode 15 and capacitor 17 is also connected to pin 6 of timer U7 and through a rheostat R70 and a resistor R55 to pin 7 of timer U7.

A capacitor C7 is connected between pins 1 and 5 of timer U7 and the negative plate of capacitor C7 is connected to the negative 12 volt power supply. In addition, the output of op amp U5b of comparator 50 is connected through line 55c and through a resistor R17 to pin 4 of timer U7. Pin 8 of timer U7 is grounded. Finally, pin 3 of timer U7, the output pin of the timer, is connected to a valve actuator subcircuit 52b shown in FIG. 5C.

Pin 4 of the timer U7 is also connected through a resistor R9 to the minus 12 volt power supply. Pin 4 is connected as well to a capacitor C12 to the positive 12 volt power supply.

The valve controller circuit 52a also includes an op amp U6. The inverting input terminal of U6 is connected to the n side of a diode D25, the p side of which is connected to the collector of transistor Q5 of comparator 50. The noninverting input of op amp U6 is connected to the junction between a resistor R31 and a resistor R3. The remaining terminals of resistors R31 and R3 are connected to the positive 12 volt power supply and ground, respectively. A feedback is provided between the output of op amp U6 and the noninverting input terminal through a feedback resistor R69. The output of op amp U6 is also connected to a resistor R13 which is in turn connected to the n side of a LED D23, the p side of which is connected to the positive 12 volt power supply.

Figure 5C:
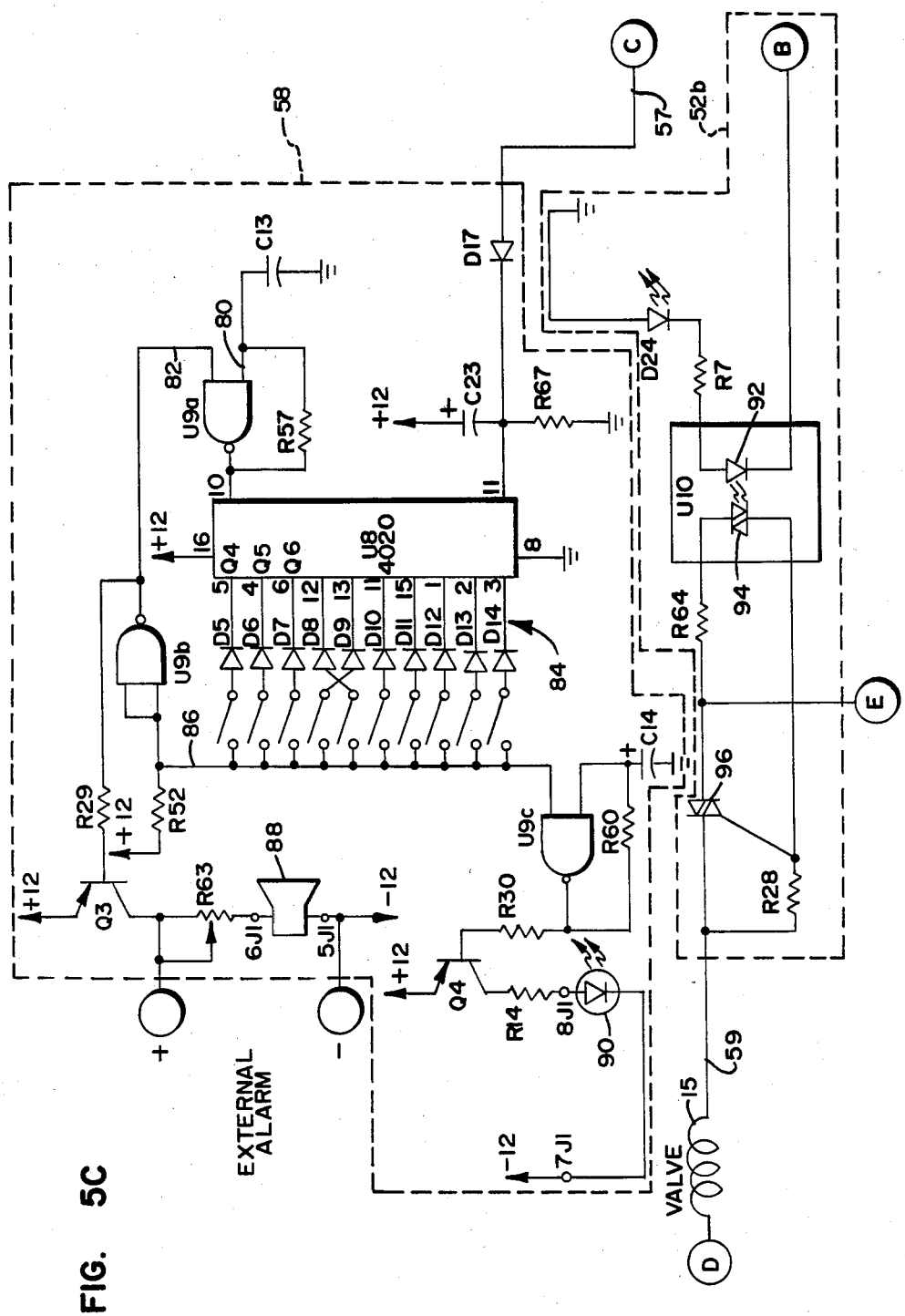
FIG. 5C is a circuit diagram illustrating a third portion of a preferred concentration controller of the type functionally diagrammed in FIG. 2.

As shown in FIGS. 2 and 5B, lines 55 and 57 connect the output of comparator circuit 50 to the alarm timer/alarm subcircuit 58. As shown in FIG. 5C, line 57 connects the output of op amp U5b of comparator circuit 50 to the p side of a diode D17 in the alarm timer/alarm subcircuit 58. The n side of diode D17 is connected to the reset pin 11 of a type 4020 binary timer U8. The reset pin 11 is also grounded through a resistor R67 and is connected to a capacitor C23 which is tied to the positive 12 volt bus. Pin 8 of counter U8 is grounded.

Pin 10 of counter U8 is connected to the output terminal of a Nand gate U9a and is also connected through a feedback resistor R57 to a first input terminal 80 of Nand gate U9a. Input terminal 80 is also connected to ground through a capacitor C13. The other input terminal 82 of Nand gate U9a is connected to the output terminal of another Nand gate U9b. The input terminals of Nand gate U9b are tied together and connected to the plus 12 volt power supply through an input resistor R52. The input terminals of Nand gate U9b are also connected by a line 86 to a diode switch network 84 made up of a number of parallel legs each having a two terminal switch and a diode. The number of seconds of allowable continuous valve actuation (corresponding to a measured conductivity less than 90% of the set point) is set by closing the appropriate switches to connect certain pins on timer U8 to the positive voltage (normally) on line 86. When the counter U8, which has an internal oscillator, reaches the binary count corresponding to the closed switches of network 84, line 86 drops in voltage which causes the output of Nand gate U9b to go into a "high" state.

The output of Nand gate U9b is connected through resistor R29 to the base of a PNP transistor Q3. The emitter of transistor Q3 is connected to positive 12 volts and the collector of transistor Q3 is connected through a resistor R63 to the first terminal of an audible alarm 88. The second terminal of audible alarm 88 is connected to the negative 12 volt power supply. Thus, when the output of Nand gate U9b goes into a high state transistor Q3 is turned on and the audible alarm 88 sounds.

Line 86 is also connected to the input of another Nand gate U9c. The second input terminal of Nand gate U9c is connected to ground through a capacitor C14 and is connected to the output of Nand gate U9c through a feedback resistor R60. The output of Nand gate U9c is also connected to the base of a PNP transistor Q4 through a resistor R30. The emitter of transistor Q4 is connected to the positive 12 volt power supply and the collector is connected to a resistor R14 which is in turn connected to the p side of an LED 90. The n side of LED 90 is connected to the negative 12 volt bus.

Referring to FIGS. 5B and 5C, the output of pin 3 of timer U7 of valve controller 52a is connected to the n side of an LED 92 imbedded in a triac driver U10. The p side of LED 92 is connected to a resistor R7 which is tied to the n side of another LED D24, and the p side of LED D24 is grounded. Triac driver U10 includes a light sensitive triac 94 which is connected on one end to a resistor R64 in series with the MT2 terminal of a triac 96, the gate of which is connected to the other terminal of optically sensitive triac 94. The gate of triac 96 is also connected through a resistor R28 to the MT1 terminal of triac 96. The MT1 terminal is finally connected by line 59 to one end of a coil which symbolizes the inductive load created by solenoid valve 15. The other end of the solenoid coil is connected to terminal 62b of power supply 60 (see FIG. 3), optionally through switch 29. Terminal MT2 to triac 96 is connected to terminal 62a of power supply 60.

OPERATION

The operation of the device shown in the Drawing, including a preferred concentration controller, can now be described. Prior to the installation of the system a preferred detergent concentration must be chosen. Once this concentration is chosen the appropriate switches of network 80 in titration amplifier 48 can be closed to select the proper gain of op amp U4b. As discussed above, the gain of op amp U4b is manually adjusted so that the output of op amp U4b is substantially equal to 5 Volts DC when the detergent concentration in the wash water is substantially 100% of the preselected concentration. The individual installing the equipment can simply refer to a table which shows the proper switch closings in network 80 corresponding to the selected detergent concentration. The correspondence between conductivity and detergent concentration is well known and such a table could readily be generated by those skilled in the art.

Once the titration amplifier 48 is properly adjusted, the alarm timer 58 should be chosen. The alarm timer U8 can be selected using the switches in network 84. The alarm timer 58 can be adjusted so that the alarm will sound anywhere between 1 second and 17 minutes following continuous valve actuation.

Following these adjustments, the dishwashing cycle can be commenced. During the dishwasher cycle, reservoir 11 will fill with wash water and conductivity cell 12 will become immersed in wash water as shown in FIG. 1. Once the sensor 12 is immersed the controller 16 can be activated, preferably by closing switch 29. The oscillator 30 then supplies a 20 Khz signal via line 31 to push-pull amplifier 32 where the signal is amplified. The potentiometer 62 of amplifier 32 can be adjusted to adjust the amplitude of the 20 Khz signal on line 33 leading to the primary coil 34, but the primary coil 34 is preferably supplied with 4 volts peak.

The primary coil 34, imbedded in the plastic sheath of conductivity cell 12, induces a voltage in the wash water and the wash water in turn induces a voltage in the secondary coil 36 in direct proportion to the conductivity of the wash water. It should be noted that the signal supplied to amplifier 38 on line 37 is not yet temperature compensated. Amplifier 38 amplifies the uncompensated signal provided by secondary coil 36 and this AC signal is provided to true full wave rectifier 40 which converts it to DC according to a well-known technique.

This DC signal is temperature compensated in the voltage divider network made up of resistors R47, R20 and temperature compensation thermistor 46. As the temperature in the wash water increases, the resistance presented by thermistor 46 decreases so that any artificial increase in conductivity as reflected on line 41 will be accounted for. That is, since the temperature compensation thermistor 46 is grounded through the temperature compensation amp 38, as its resistance decreases due to the temperature increases, voltage created solely by temperature increases will be removed from the signal which is provided to temperature compensation amplifier 42. Temperature compensation amplifier 42 simply amplifies the temperature compensated concentration signal and provides it to the titration amplifier 48 and to the test point 44.

The function of titration amplifier 48 has been described above. The gain of the amplifier 48 is selected so as to produce 5 Volts DC on line 35 when the concentration of detergent in the wash water in reservoir 11 is equal to the preselected concentration. If the voltage on line 35 is indeed 5 volts, op amp U6 will divert any charging current provided by transistor Q5. If this is the case, capacitor 17 of valve controller 52a will not charge and timer U7 will not activate the valve 15. Op amp U6 will also cause LED D23 to activate under these conditions.

If the voltage on line 35 is less than 4.5 volts, this indicates that the concentration of detergent in the wash water is less than 90% of the preselected concentration. In this case, the output of comparator op amp U5b goes negative which overrides timer U7, via pin 4, so as to eliminate the timing sequence and continuously turn on solenoid valve 15 by activating output pin 3. Of course, the negative output of op amp U5b is also directed to the alarm timer/alarm circuit 58 through line 57. If the valve 15 is activated for too long a period, timer U8 times out which causes the output of Nand gate U9b of alarm circuit 58 to go into its low state. As discussed above, this causes transistor Q3 to conduct which causes the audible alarm 88 to sound.

When the output of Nand gate U9b is high, Nand gate U9a oscillates at 8 hz and the output of Nand gate U9c provides the clock signal for IC U8. The oscillation frequency is determined by the RC combination of R57 and C13.

When the counter IC U8 has reached the preselected time setting, line 86 goes high which causes the output of gate U9b to go low. This in turn disables gate U9c from oscillating.

In like manner, when line 86 is high, gate U9c oscillates to cause LED 90 to blink.

When the concentration exceeds 90%, timer U8 is reset and gate U9a begins to oscillate. Once the reset signal to timer U8 is released or brought low due to the measured concentration being less than 90% of the desired concentration, timer U8 will begin to once again count to the preselected value.

The timer U8 is reset when the voltage on line 57 changes from negative to positive. This corresponds to a detergent concentration greater than 90% of the set point.

The third possible condition is that the voltage on line 35 is between 4.5 and 5 Volts DC. In this case, the output of op amp U5a is proportional to the difference between the voltage on line 35 and the reference voltage corresponding to full scale. The output of op amp U5a causes transistor Q5 of comparator 52 to conduct to a degree directly proportional to this difference. As transistor Q5 becomes more conductive, capacitor C17 will charge in a shorter period of time. Conversely, capacitor C17 will take longer to charge if transistor Q5 is less conductive.

The charge time of capacitor C17 corresponds to the off time for the solenoid valve 15. The on time for the valve 15 is selectable from 2 seconds to 17 seconds by adjusting potentiometer R70. The capacitor C17 is discharged during the on time of valve 15 through R70 and R55. Thus, following the preset on time for valve 15, the capacitor C17 begins to charge anew based upon the conductivity of transistor Q5.

As the conductivity of the wash water 11 approaches the preselected conductivity, the voltage at the output of op amp U5a of comparator 50 will decrease and this causes the conductivity of Q5 to decrease which in turn increases the charge time of capacitor C17. This creates a longer off time for valve 15 and tends to eliminate overshoot in the corrective action.

When the conductivity of the wash water reaches 100% of the set point, op amp U6 diverts any charging currents and the valve 15 will remain closed until the concentration again drops unacceptably low. Since the voltage and the emitter of transistor Q5 approaches zero volts under these conditions, LED D23 is activated indicating that the wash water has a conductivity equal to 100 percent of the set point.

The specifications for preferred components of the circuit shown in the Drawing are given below:

| COMPONENT | DESCRIPTION |
| --- | --- |
| R1, 2 | 47 OHM, 5%, ¼ W |
| R4, 5 | 150 OHM, 5%, ¼ W |
| R6 | 390 OHM, 5%, ¼ W |
| R7, 64 | 470 OHM, 5%, ¼ W |
| R8 | 510 OHM, 5%, ¼ W |
| R3, 9, 27 | 1K OHM, 5%, ¼ W |
| R10-14 | 2K OHM, 5%, ¼ W |
| R15, 66 | 2.7K OHM, 5%, ¼ W |
| R18 | 4.7K OHM, 5%, ¼ W |
| R19 | 5.1K OHM, 5%, ¼ W |
| R20, 21 | 7.5K OHM, 5%, ¼ W |
| R22 | 8.2K OHM, 5%, ¼ W |
| R17, 23-26, 28-30, 55, 67 | 10K OHM, 5%, ¼ W |
| R32 | 13K OHM, 5%, ¼ W |
| R33, 35 | 15K OHM, 5%, ¼ W |
| R34 | 18K OHM, 5%, ¼ W |
| R36-39 | 20K OHM, 5%, ¼ W |
| R40, 41 | 24K OHM, 5%, ¼ W |
| R16 | 27K OHM, 5%, ¼ W |
| R42 | 30K OHM, 5%, ¼ W |
| R43 | 39K OHM, 5%, ¼ W |
| R44, 45 | 51K OHM, 5%, ¼ W |
| R46 | 62K OHM, 5%, ¼ W |
| R47 | 68K OHM, 5%, ¼ W |
| R48-50, 52, 60 | 100K OHM, 5%, ¼ W |
| R53 | 120K OHM, 5%, ¼ W |
| R57 | 160K OHM, 5%, ¼ W |
| R54 | 240K OHM, 5%, ¼ W |
| R58, 59, 68 | 1 M OHM, 5%, ¼ W |
| R69 | 3.3 M OHM, 5%, ¼ W |
| R31, 56 | 510K OHM, 5%, ¼ W |
| R65 | 220 OHM, 5%, 2 W |
| R61 | 2K OHM |
| R62 | 5K OHM |
| R63 | 20K OHM |
| R70 | 100K OHM |
| C1 | 220 PFD, 200 V |
| C2 | 470 PFD, 200 V |
| C3 | .002 MFD, 100 V |
| C4-7 | .1 MFD, 50 V |
| C9-11 | .2 MFD, 50 V |
| C13 | .47 MFD, 35 V |
| C22, 23 | 1 MFD, 35 V |
| C12, 14-16 | 10 MFD, 25 V |
| C18, 19 | 22 MFD, 35 V |
| C17 | 220 MFD, 10 VDC |
| C21 | 470 MFD, 10 VDC |
| C20 | 1000 MFD, 50 VDC |
| D1-4 | 1 AMP, 200 PRV |
| D5-19, 25 | 1N4447 |
| D20-22 | 6.2 VOLT ZENER, 1N753A |
| U1 | QUAD OP-AMP, TL084 |
| U2-5 | DUAL OP-AMP, TL082 |
| U6 | COMPARATOR, LM311N |
| U7 | TIMER, LM555 |
| U8 | COUNTER, CD4020 |
| U9 | QUAD NAND GATES, CD4093 |
| U10 | TRIAC DRIVER, 3021 |
| U11 | 24 VDC REGULATOR, 7824 |
| U12 | 12 VDC REGULATOR, 7824 |
| D23, 24 | LIGHT EMITTING DIODES |
| Q1 | NPN, 2N2222A |
| Q2-5 | PNP, 2N2907 |
| Q6 | TRIAC, 400 V, 3 AMP |

It should be emphasized that the present invention is not limited to any particular components, materials or configurations and modifications of the invention will be apparent to those skilled in the art in light of the foregoing description. This description is intended to provide specific examples of individual embodiments which clearly disclose the present invention. Accordingly, the invention is not limited to these embodiments or to the use of elements having the specific configurations and shapes as presented herein. All alternative modifications and variations of the present invention which fall within the spirit and broad scope of the appended claims are included.

We claim:

1. An apparatus for controlling the concentration of a detergent solution comprising:
(A) means for providing a concentration signal representing the concentration of the solution comprising a primary coil and a secondary coil, wherein when the coils are immersed in the solution the solution provides an electrical coupling between the coils;
(B) means for changing the concentration of the solution; and
(C) means for controlling the concentration changing means comprising:
(1) means for comparing the concentration signal with a reference signal representing a preselected desired concentration and generating an error signal representing the difference therebetween; and
(2) means for activating the concentration changing means in response to the error signal, wherein the concentration changing means comprises means for increasing the concentration of the solution and wherein the activating means comprises:

(a) timing means for:
  (i) continuously activating the concentration increasing means when the error signal indicates that the concentration of the solution is less than a preselected percentage of the desired concentration;
  (ii) not activating the concentration increasing means when the error signal indicates that the concentration of the solution is substantially equal to the desired concentration; and
  (iii) periodically activating the concentration increasing means when the error signal indicates that the concentration of the solution is between the desired concentration and the preselected percentage of the desired concentration, wherein the rate at which the concentration increasing means is activated is directly related to the difference between the actual concentration and the desired concentration, whereby overshoot is substantially eliminated; and
(b) alarm means for determining whether the concentration increasing means has been continuously activated for an excessive period of time.

2. The apparatus of claim 1, wherein the magnitude of the error signal is directly related to the difference between the concentration of the solution and the desired concentration, and wherein the timing means comprises a capacitor which is subject to charging by the error signal, wherein the concentration increasing means is not activated during the period of time that the capacitor is charging, whereby the concentration increasing means is not activated for a period of time directly dependent on the magnitude of the error signal, and is otherwise activated.

3. An apparatus for controlling the concentration of a detergent solution comprising:

(A) means for providing a concentration signal representing the concentration of the solution comprising a primary coil and a secondary coil, wherein when the coils are immersed in the solution the solution provides an electrical coupling between the coils;
(B) means for changing the concentration of the solution; and
(C) means for controlling the concentration changing means comprising:
  (1) means for comparing the concentration signal with a reference signal, the reference signal comprising a first reference signal representing 100 percent of a desired concentration and a second reference signal representing a preselected lower percentage of the same desired concentration, and generating an error signal representing the difference therebetween; and
  (2) means for activating the concentration changing means in response to the error signal, wherein the comparing means comprises first and second comparators, wherein:
    (a) the first comparator compares the concentration signal to the first reference signal and the second comparator compares the concentration signal to the second reference signal, wherein when the second comparator indicates that the measured concentration is less than the preselected lower percentage of the desired concentration, the concentration changing means is continuously activated;
    (b) when the second comparator indicates that the measured conductivity is greater than the preselected lower percentage of the desired concentration but the first comparator indicates that the measured concentration is less than the desired concentration, the activating means periodically activates the concentration changing means at a rate which is directly related to the magnitude of the error signal; and
    (c) when the first comparator indicates that the concentration is substantially equal to the desired concentration, the activating means does not activate the concentration changing means.

4. The apparatus of claim 3, wherein the preselected lower percentage is 90%.

5. An apparatus for controlling the concentration of a wash water solution suitable for use in a ware washing machine by controlling the flow of a concentrated solution of detergent and water to the wash water solution, comprising:

(a) means for producing a 100% reference signal representing a preselected desired wash water concentration;
(b) means for producing a 90% reference signal representing a concentration 90% of the desired concentration;
(c) means for providing an amplified temperature compensated concentration signal, comprising:
  (i) a primary coil;
  (ii) a secondary coil;
  (iii) a thermistor operatively connected to the secondary coil for compensating for changes in the temperature of the wash water solution, wherein when the coils and the thermistor are immersed in the wash water solution, the secondary coil produces an uncompensated signal indicative of the conductivity of the wash water solution and the thermistor produces a temperature compensated concentration signal by changing the uncompensated conductivity signal in inverse relation to the temperature of the wash water solution; and
  (iv) an amplifier for adjustably amplifying the temperature compensated signal to produce the amplified temperature compensated concentration signal, wherein the gain of the amplifier can be adjusted so that the amplified signal is equal to the 100% reference signal when the concentration of the wash water solution is equal to the desired concentration;
(d) a first comparator for comparing the amplified concentration signal with the 100% reference signal;
(e) a second comparator for comparing the amplified concentration signal with the 90% reference signal, wherein the comparators produce an error signal indicative of the difference between the measured ware washing solution concentration and the desired concentration;
(f) means for increasing the concentration of the wash water solution comprising a normally closed valve for controlling the flow of the concentrated solution of detergent and water to the wash water solution;

(g) means responsive to the error signal for:
  (i) continuously activating the normally closed valve when the error signal indicates that the concentration of the wash water solution is less than that represented by the 90% concentration signal;
  (ii) not activating the normally closed valve when the error signal indicates that the concentration of the solution is substantially equal to the desired concentration; and
  (iii) periodically activating the normally closed valve when the error signal indicates that the concentration of the wash water solution is between the desired concentration and 90% of the desired concentration, wherein the rate at which the normally closed valve is activated is directly related to the difference between the actual concentration and the desired concentration, whereby overshoot is substantially eliminated; and
(h) alarm means for determining whether the normally closed valve has been continuously activated for an excessive period of time.

6. A washing apparatus comprising:
(A) means for containing a washing solution
(B) means for providing a concentration signal representing the concentration of the solution comprising a primary coil and a secondary coil, wherein when the coils are immersed in the solution the solution provides an electrical coupling between the coils;
(C) means for changing the concentration of the solution; and
(D) means for controlling the concentration changing means comprising:
  (1) means for comparing the concentration signal with a reference signal representing a preselected desired concentration and generating an error signal representing the difference therebetween; and
  (2) means for activating the concentration changing means in response to the error signal, wherein the concentration changing means comprises means for increasing the concentration of the solution and wherein the activating means comprises:
    (a) timing means for:
      (i) continuously activiating the concentration increasing means when the error signal indicates that the concentration of the solution is less than a preselected percentage of the desired concentration;
      (ii) not activating the concentration increasing means when the error signal indicates that the concentration of the solution is substantially equal to the desired concentration; and
      (iii) periodically activating the concentration increasing means when the error signal indicates that the concentration of the solution is between the desired concentration and the preselected percentage of the desired concentration, wherein the rate at which the concentration increasing means is activated is directly related to the difference between the actual concentration and the desired concentration, whereby overshoot is substantially eliminated;
    (b) alarm means for determining whether the concentration increasing means has been continuously activated for an excessive period of time.

7. The apparatus of claim 6, wherein the magnitude of the error signal is directly related to the difference between the concentration of the solution and the desired concentration, and wherein the timing means comprises a capacitor which is subject to charging by the error signal, wherein the concentration increasing means is not activated during the period of time that the capacitor is charging, whereby the concentration increasing means is not activated for a period of time directly depending on the magnitude of the error signal, and is otherwise activated.

8. A washing apparatus comprising:
(A) means for containing a washing solution;
(B) means for providing a concentration signal representing the concentration of the solution comprising a primary coil and a secondary coil, wherein when the coils are immersed in the solution the solution provides an electrical coupling between the coils;
(C) means for changing the concentration of the solution; and
(D) means for controlling the concentration changing means comprising:
  (1) means for comparing the concentration signal with a reference signal, the reference signal comprising a first reference signal representing 100 percent of a desired concentration and a second reference signal representing a preselected lower percentage of the same desired concentration, and generating an error signal representing the difference therebetween; and
  (2) means for activating the concentration changing means in response to the error signal, wherein the comparing means comprises first and second comparators, wherein:
    (a) the first comparator compares the concentration signal to the first reference signal and the second comparator compares the concentration signal to the second reference signal, wherein when the second comparator indicates that the measured concentration is less than the preselected lower percentage of the desired concentration, the concentration changing means is continuously activated;
    (b) when the second comparator indicates that the measured conductivity is greater than the preselected lower percentage of the desired concentration but the first comparator indicates that the measured concentration is less than the desired concentration, the activating means periodically activates the concentration changing means at a rate which is directly related to the magnitude of the error signal; and
    (c) when the first comparator indicates that the concentration is substantially equal to the desired concentration, the activiating means does not activate the concentration changing means.

9. The apparatus of claim 8, wherein the preselected lower percentage is 90%.

10. A ware washing apparatus comprising:
(a) a reservoir for containing the ware washing solution;
(b) means for producing a 100% reference signal representing a preselected desired wash water concentration;
(c) means for producing a 90% reference signal representing a concentration 90% of the desired concentration;
(d) means for providing an amplified temperature compensated concentration signal, comprising:
  (i) a primary coil;
  (ii) a secondary coil;
  (iii) a thermistor operatively connected to the secondary coil for compensating for changes in the temperature of the wash water solution, wherein when the coils and the thermistor are immersed in the wash water solution, the secondary coil produces an uncompensated signal indicative of the conductivity of the wash water solution and the thermistor produces a temperature compensated concentration signal by changing the uncompensated conductivity signal in inverse relation to the temperature of the wash water solution; and
  (iv) an amplifier for adjustably amplifying the temperature compensated signal to produce the amplified temperature compensated concentration signal, wherein the gain of the amplifier can be adjusted so that the amplified signal is equal to the 100% reference signal when the concentration of the wash water solution is equal to the desired concentration;
(e) a first comparator for comparing the amplified concentration signal with the 100% reference signal;
(f) a second comparator for comparing the amplified concentration signal with the 90% reference signal, wherein the comparators produce an error signal indicative of the difference between the measured ware washing solution concentration and the desired concentration;
(g) means for increasing the concentration of the wash water solution comprising a normally closed valve for controlling the flow of the concentrated solution of detergent and water to the wash water solution;
(h) means responsive to the error signal for:
  (i) continuously activating the normally closed valve when the error signal indicates that the concentration of the wash water solution is less than that represented by the 90% concentration signal;
  (ii) not activating the normally closed valve when the error signal indicates that the concentration of the solution is substantially equal to the desired concentration; and
  (iii) periodically activating the normally closed valve when the error signal indicates that the concentration of the wash water solution is between the desired concentration and 90% of the desired concentration, wherein the rate at which the normally closed valve is activated is directly related to the difference between the actual concentration and the desired concentration, whereby overshoot is substantially eliminated; and
(i) alarm means for determining whether the normally closed valve has been continuously activated for an excessive period of time.

11. An appartus for controlling the concentration of a detergent solution comprising:
(A) means for providing a concentration signal representing the concentration of the solution comprising a primary coil and a secondary coil, wherein when the coils are immersed in the solution the solution provides an electrical coupling between the coils;
(B) means for changing the concentration of the solution; and
(C) means for controlling the concentration changing means comprising:
  (1) means for comparing the concentration signal with a reference signal representing a preselected desired concentration and generating an error signal representing the difference therebetween; and
  (2) means for activating the concentration changing means in response to the error signal, wherein the concentration changing means comprises means for increasing concentration of the solution and wherein the activating means comprises:
    (a) timing means for;
      (i) continuously activiating the concentration increasing means when the error signal indicates that the concentration of the solution is less than a preselected percentage of the desired concentration;
      (ii) not activating the concentration increasing means when the error signal indicates that the concentration of the solution is substantially equal to the desired concentration; and
      (iii) periodically activating the concentration increasing means when the error signal indicates that the concentration of the solution is between the desired concentration and the preselected percentage of the desired concentration, whereby overshoot is substantially eliminated; and
    (b) alarm means for determining whether the concentration increasing means has been continuously activated for an excessive period of time.

12. The apparatus of claim 11, wherein the magnitude of the error signal is directly related to the difference between the concentration of the solution and the desired concentration, and wherein the timing means comprises a capacitor which is subject to charging by the error signal, wherein the concentration increasing means is not activated for a period of time directly depending on the magnitude of the error signal, and is otherwise activated.

* * * * *